United States Patent [19]

Katz

[11] 4,325,386

[45] Apr. 20, 1982

[54] MEANS FOR TREATING SYMPTOMS OF MENIERE'S DISEASE OR THE LIKE

[76] Inventor: Jay W. Katz, 328 Cove Neck Rd., Oyster Bay, N.Y. 11771

[21] Appl. No.: 97,707

[22] Filed: Nov. 27, 1979

[51] Int. Cl.³ ............................................. A61B 5/04
[52] U.S. Cl. ................................... 128/733; 128/745; 128/746; 128/401
[58] Field of Search ................ 128/733, 746, 401, 745

[56] References Cited

U.S. PATENT DOCUMENTS

| | | | |
|---|---|---|---|
| 3,000,271 | 9/1961 | Harvey et al. | 128/746 X |
| 3,563,231 | 2/1971 | Ducote et al. | 128/746 X |
| 4,023,561 | 5/1977 | Servos | 128/746 X |
| 4,106,493 | 8/1978 | Proctor et al. | 128/401 X |
| 4,106,496 | 8/1978 | Proctor et al. | 128/401 X |

Primary Examiner—Kyle L. Howell

[57] ABSTRACT

Binaural pressure-response differentials which are symptomatic of vertigo, particularly Meniere's disease, are therapeutically treated by establishing a thermal environment externally local to one ear drum with respect to the other, in the polarity sense which reduces such response differentials. For cases in which a nystagmus condition has developed, the invention utilizes observed nystagmus rate to provide automatic control of the locally applied thermal environment, in magnitude and duration suited to observed abatement of the nystagmus condition. Portable apparatus of the invention enables the patient to apply his own therapy whenever he senses onset symptoms of an attack.

15 Claims, 6 Drawing Figures

MEANS FOR TREATING SYMPTOMS OF MENIERE'S DISEASE OR THE LIKE

BACKGROUND OF THE INVENTION

The invention pertains to a method for treating a vertigo or the like attack, as when afflicted with Meniere's disease.

Meniere's disease is a significant health problem, having an incidence now identified of 46 per 100,000 population, but the disease has eluded successful treatment for more than the century which has lapsed since Dr. Meniere described and identified the malady.* He observed that an otherwise perfectly healthy "auditory apparatus . . . can suddenly become the seat of functional disorders consisting in various kinds of noises"; that "these functional disorders . . . can give rise to incidents said to be cerebral, such as vertigo, giddiness, unsteady walk, spinning and falling, in addition to which they are accompanied by nausea, vomiting and a fainting state"; and that "these incidents, which are intermittent in form, are soon followed by ever increasing deafness." Many efforts have since been made to treat if not to solve the problem; and the various classes of medical, surgical and drug therapies have recently been summarized by Professor Schuknecht**, but no effective treatment or solution has yet been reported, and the professor concludes that it "is encumbent on all physicians to assess their personal therapeutic approaches to the treatment of Meniere's disease in light of the current knowledge and to keep abreast of new developments in this rapidly moving field of research."

*Gaz. Med. Paris, 16:597 to 601, 1861 [English translation by M. Atkinson, Acta Otolaryngol. (Suppl. 162)].
**Schuknecht, H. F., "A Critical Evaluation of Treatments for Meniere's Disease," J.C.E.O.R.L. & Allergy, October, 1978, pp. 15-30.

Nystagmus is one of the symptoms of an attack of Meniere's disease, and it has been reported that "caloric irrigation during an attack can reverse the direction of the nystagmus, eliminate it, decrease its amplitude, not affect it, or increase its amplitude, depending upon the direction and magnitude of the nystagmus, and the duration and temperature of the irrigant."*** But the apparatus to perform such irrigation and to observe the nystagmus is complex laboratory equipment, not in any sense portable or adapted for use other than by and under control of the physician. Moreover, attacks of Meniere's disease come infrequently and unpredictably, so that the opportunity for the physician even to observe, if not to treat, his patient during the onset portion of an attack, which attack may last several hours, is so rare as to have thus far effectively precluded such treatment for the patient.

*** Paparella and Schumrich, Otolaryngology, Vol. II, p.441.

BRIEF SUMMARY OF THE INVENTION

It is an object of the invention to provide means whereby caloric irrigation may be available to an afflicted individual for timely, safe and effective treatment of an attack of the character indicated.

It is a specific object to meet the above object with portable apparatus which the individual may employ for his own therapy, upon his recognition of the onset of an attack.

Another object is to achieve the above objects with apparatus having simplified control means whereby the individual may selectively modify the temperature of the irrigating fluid, in accordance with his subjective determination of comfort and dissipation of the attack.

It is also an object to meet the above objects with automatic control of the nature and duration of exposure to caloric irrigation.

A further object is to achieve the preceding object using a detected nystagmus function as the primary controlling factor.

Another specific object is to provide simple battery-powered electrode structure for removable use by the individual to enable electrical monitoring and control of his current nystagmus condition.

In the forms to be described, the invention accomplishes the foregoing objects and various further features in the context of caloric-irrigation apparatus which relies upon a light-weight head-supported nozzle having flexible connection to a portable housing (a) for a self-contained source of caloric-irrigation fluid and (b) for a self-contained source of energy for controlled heating of irrigating fluid. In one embodiment, simple manual controls enable the individual to adjust temperature and flow rate, to suit his subjective determination of comfort and relief. In another embodiment, an easily applied electrode "mask" enables him to rely on currently detected electronystagmogram signals to automatically control temperature and/or flow rate of the irrigating fluid. In a further embodiment, each ear is subjected to a different caloric irrigation, to the end that inner-ear pressure-response differentials are more quickly reduced.

DETAILED DESCRIPTION

The invention will be illustratively described for several embodiments, in conjunction with the accompanying drawings, in which:

FIG. 4 is a fragmentary diagram schematically showing nystagmus-monitoring means for use with either of the embodiments of FIGS. 1 and 2; and FIG. 5 is a plan view of a disposable single-use electrode device for alternative employment in the nystagmus-monitoring means of FIG. 4.

Figure 1:
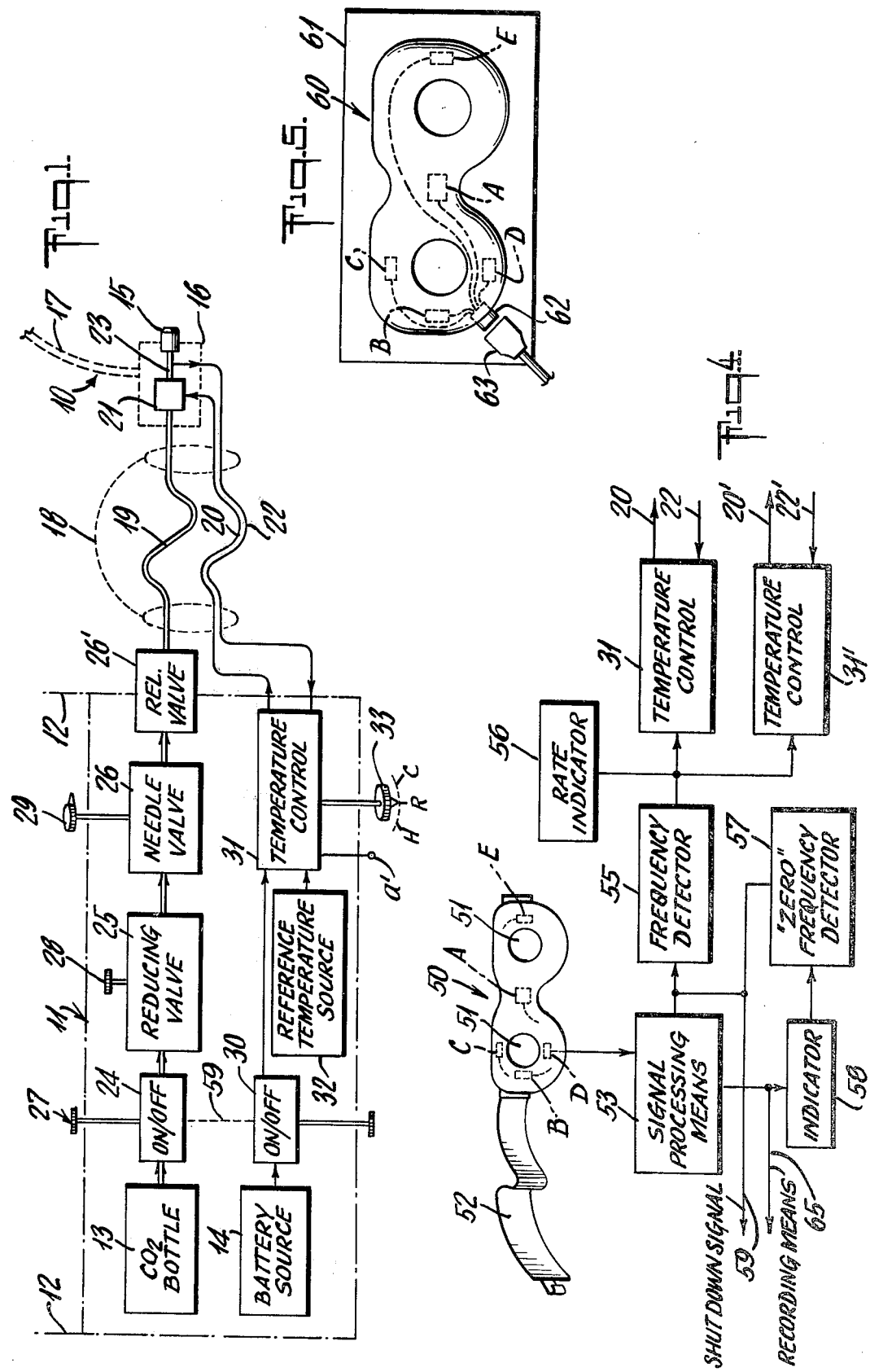
FIG. 1 is a simplified diagram schematically showing components of a preferred embodiment of the invention.

The embodiment of FIG. 1 comprises a head-mounted portable unit 10 and a hand or otherwise portable unit 11, which may be shoulder-slung, as suggested by flexible straps 12. Unit 11 is a supply and control casing intended for use to combat a single attack; it is therefore preferably equipped with a replaceable or rechargeable bottle 13 for pressurized caloric-irrigation fluid and with a replaceable or rechargeable battery source 14 of electric power.

The head-mounted unit 10 comprises a discharge nozzle 15 configured to fit the ear and to discharge a flow of caloric-irrigation fluid, such as suitably heated air or other gas, with irrigating incidence at or in the immediate vicinity of the tympanic membrane of the ear. An ear-adapting mount 16 carries nozzle 15, and a suitably compliant arched band 17 supports mount 16 at one end and is in turn referenced to and over the top of the head, in the manner of a telephone headset.

A flexible connection, suggested by spaced phantom ovals 18, connects the units 10–11 and is shown to include an irrigating-gas line 19, which may be a length of plastic tubing. The flexible connection also includes wiring 20 for a first or power-supply circuit to heating means 21, and wiring 21 for a second or temperature-sensing circuit having a suitably mounted sensing element, such as a bead thermistor 23, at nozzle 15 or at the short fluid connection between heating means 21 and nozzle 15.

The legend at 13 in FIG. 1 suggests pressurized carbon dioxide as the source of irrigation fluid, but it will be understood that this was selected for its ready commercial availability, and that similarly pressurized other gases such as air or nitrogen could also serve. Within the case of unit 11, the connection of pressure-fluid source 13 to flexible tubing 19 is shown to serially include an ON/OFF valve 24, a reducing valve 25 and a needle valve 26, all to the end that a steady controlled flow of irrigating fluid will be passed via nozzle 15 throughout a single use, which may be in the order of five minutes to an hour in duration, depending on the user's response to the treatment. Valve 24 is shown with an external ON/OFF button control 27; adjustment means 28 for setting the reducing valve 25 is shown pre-set within the case 11; and an external knob 29 of needle valve 26 enables the user to make a flow-rate adjustment, preferably within relatively narrow safe-operating limits. Finally, at unit 11, a relief valve 26' is set to vent pressure fluid to the atmosphere in the unlikely event of pressure, supplied to line 19, rising to a predetermined limit of safety; in other words, relief valve 26' is set for such safety venting at onset of line (19) pressure just above the upper limit of the relatively narrow safe-operating range.

On the electrical side, within the casing 11, an ON/OFF switch 30 is interposed between battery 14 and temperature-control means 31. The means 31 may include a bridge circuit differentially responsive to a sensed heat-signal level in line 22, in reference to a reference-temperature signal level available from suitable means 32. Means 31 will further be understood to include means responsive to magnitude and polarity of the instantaneous difference between the sensed heat-signal level and the reference-signal level, for regulating the instantaneous current flow via circuit 20 and through 21, in the sense to achieve a perceived balance through temperature offset of one ear with respect to the other, selective control of such temperature offset being subject to external setting at a knob 33. Knob 33 is shown with a pointer, readable against a fixed scale between hot and cold limits, suggested by legends H and C, a central or reference temperature being suggested by the legend R.

In use, i.e., with valve 24 open, a relatively slow flow of irrigating fluid passes via tube 19 and nozzle 15. Without heat supplied at 21, the flowing gas will be cold, much colder than body temperature, due to cooling which results from expansion of the gas upon its release from pressurized storage. The heating means 21 is used to heat the irrigating fluid as necessary to bring it to nozzle discharge at substantially the temperature selected by adjustment of knob 33. With body temperature as the reference temperature (R), a positioning of knob 33 toward the C limit (as shown in FIG. 1) will mean automatic heating of the irrigating fluid flow to a point on the cool side of body temperature, while a positioning of knob 33 toward the H limit will mean automatic heating of the irrigating fluid flow to a point on the warm side of body temperature.

When an individual with Meniere's disease begins to recognize symptoms of an attack, he need only reach for his portable equipment of FIG. 1 and apply the unit 10 to his head, it being observed that his doctor will have instructed him (a) which ear is to receive nozzle 15 and (b) whether to make a temperature setting on the H or C side of the body-heat reference R. What had been a vertigo symptom involving a pressure-response differential or unbalance as between the two inner ears is now perceived by the affected inner ear as a restoration of balance (reduction in pressure-response differential), so that the chain of events which would normally be triggered by the unbalance at the time of onset of the attack will no longer be enabled to proceed. The attack and its consequences have thus been staved off, and the afflicted individual need only recharge or replace his sources 13-14 and keep his portable equipment handy, for use at onset of the next attack, which may not occur for a matter of weeks or months. He has meanwhile saved himself the trauma and possible lasting consequences of a full attack, and has involved himself for a matter of minutes instead of what otherwise could have been a matter of hours.

Figure 2:
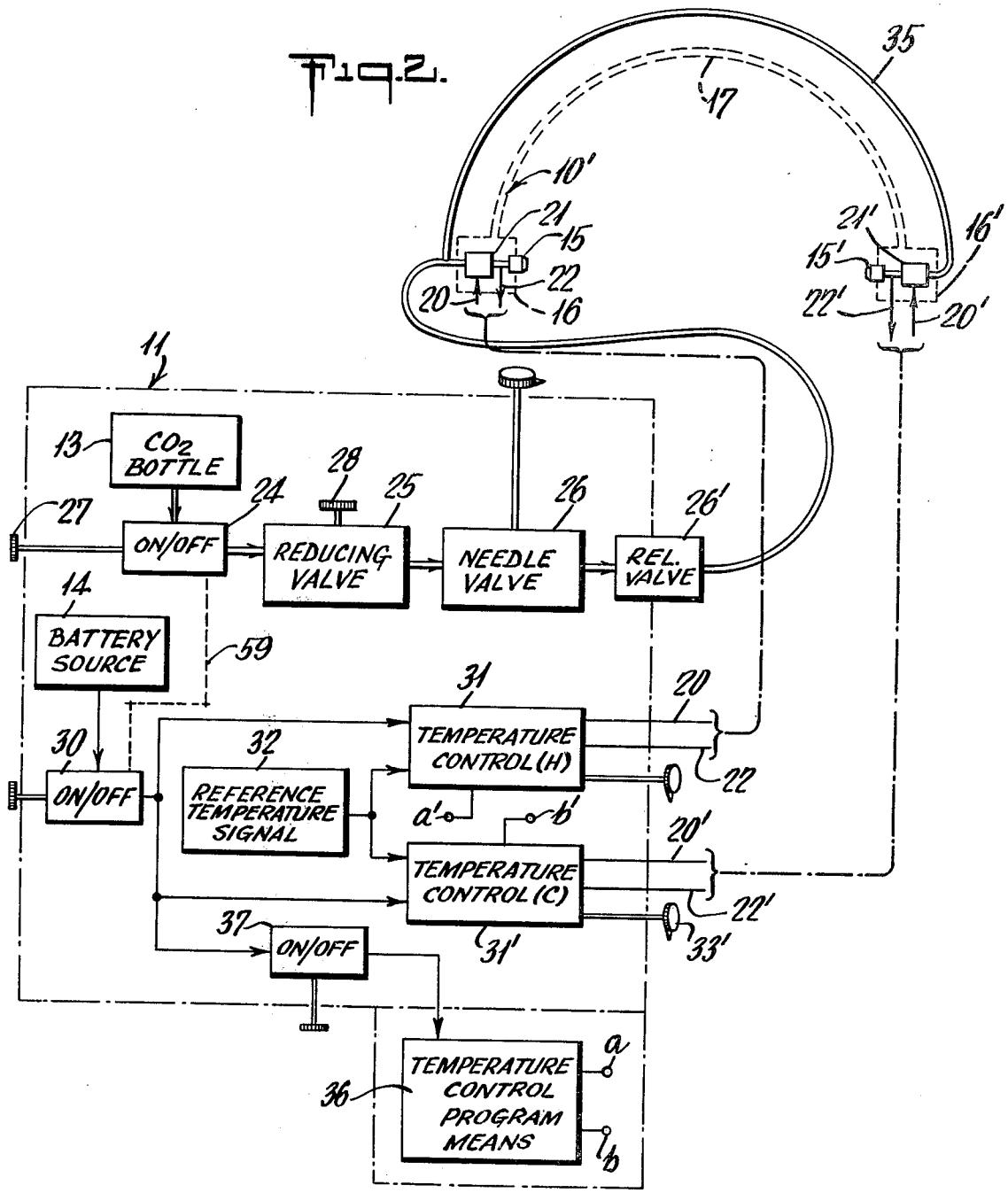
FIG. 2 is a similar diagram showing a second embodiment.

In the embodiment of FIG. 2, most of the elements of FIG. 1 are recognizable and therefore the same reference numbers are employed, where appropriate. The principal difference in FIG. 2 is that the head-mounted unit 10' has a second irrigation nozzle 15' carried by a mount 16' for adapted positioning to irrigate the other ear. The single tube 19 supplies a regulated irrigating flow to nozzle 15 via heating means 21 and, in addition, supplies a similar flow to nozzle 15' via its associated heating means, the branch-tube connection 35 from tube 19 to heating means 21' being inconspicuously conformed to and supported by the compliant head band 17.

In the arrangement of FIG. 2, the control of temperature at heating elements is preferably coordinated to establish substantially equal but oppositely polarized temperature offsets at the respective ear-irrigating locations, the offsets being with respect to body temperature, the reference temperature. It is possible that in some cases the inner-ear response to irrigating temperature change may be non-linear, in which case the magnitude of temperature offset in one polarity sense with respect to the reference may be different from that in the opposite polarity sense, but it will be understood that such non-linear circumstances may be compensated in design and/or prealignment of the respective temperature control circuits 31—31', both of which are served by the same source 14 and by the same reference-temperature signal means 32, while heating-supply and heat-sensing functions for the respective nozzle flows are independently served by the circuits 20-22 to control means 31 and by the circuits 20'-22' to control means 31'.

Operation and use of the FIG. 2 arrangement is generally as described for FIG. 1, except for the fact that independently controlled heating functions for the respective ears involve opposite temperature offsets with respect to body temperature. For example, to achieve a perceived balance between unbalanced ear responses at onset of an attack, the temperature control for discharge from nozzle 15 may need to be about 10 degrees above body temperature, while the temperature control for discharge from nozzle 15' may need to be about 10 degrees below body temperature.

Thus far, apparatus of FIGS. 1 and 2 has been described for the circumstance that the individual controls his own starting and stopping of instrument functions, as well as the flow rate and magnitude of temperature offset of one ear's exposure with respect to the other's. In certain cases, the individual may not have timely caught the onset conditions, so that a companion may have to mount and operate the instrument. To aid in this circumstance, FIG. 2 is shown to further include, at the portable case 11, suitable temperature-control program means 36, available by operation of an ON/OFF switch 37 and having first output connections a—a' to govern control means 31 and second output connections b—b' to govern control means 31'. A simple preset timing function, for example, 10 minutes ON, and then OFF, may be all that is needed in terms of automatic control via program means 36. On the other hand, program means 36 will be understood also to provide selective variation of the respective heating controls, as illustrated by the respective curves of FIGS. 3a and 3b.

Figure 3A:
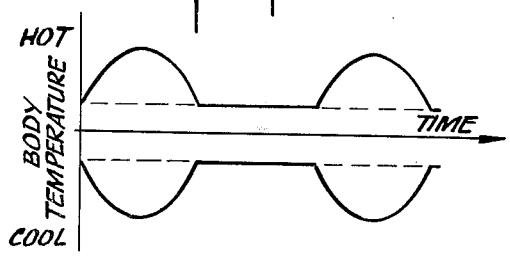
FIGS. 3a and 3b are similar graphical plots of temperature as a function of time, for two optional employments of the embodiment of FIG. 2.
Figure 3B:
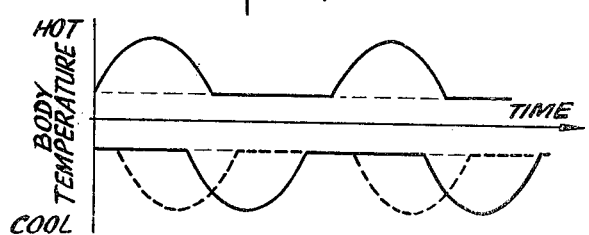

In FIG. 3a, the temperature control program means 36 determines a recurrent cycle of pulses, each pulse being say of two minutes duration, each pulse being characterized by a rise (above body temperature) and fall (to body temperature) for irrigation of one ear, and by a fall (below body temperature) and rise (to body temperature) for irrigation of the other ear. In FIG. 3a, such temperature-offset modulations are co-phasal at the respective ears, and in FIG. 3b they are in substantial phase offset; approaching phase interlace (solid lines) and in substantially quadrature phase (dashed lines). It will be understood that the program means 36 may be set for predetermined dwell time between pulses, and for final automatic shut off after a preset time for pulsed heating of the respective irrigation flows.

FIG. 4 illustrates additional components which may be part of the portable apparatus, to incorporate detected nystagmus behavior as a control factor in determining the extent of temperature offset control, at 31 in FIG. 1 or at 31—31' in FIG. 2. Basic nystagmus behavior data are derived via paired electrodes applied to facial skin near the eyes and responding to voltage changes associated with eyeball movement. More specifically, a face mask 50 with or without eye apertures 51 includes a strap 52 with suitable fastener means to establish sufficient hoop tension around the head to hold the mask in place, at general alignment with the eyes. Thus aligned, a first pair of electrodes A–B is held in contact with the skin at horizontally spaced locations on opposite sides of one eye, and a second pair of electrodes C–D is similarly held at vertically spaced locations on opposite sides of the same eye. For check-out purposes, a fifth electrode E is shown outside the other eye for pairing with electrode A to observe nystagmus movement of the other eye. Each of the electrodes A through E will be understood to have its own separate electrical connection to switching, bridge-circuit, differential-amplifier and the like contents of signal-processing means 53 carried within the supply case 11, these electrode connections being via separate conductors of a flexible cable connection 54. The construction of signal-processing means 53 forms no part of the present invention, and it suffices to note that for the particular selected pair of electrodes (usually the pair A–B or the pair A–E), a recurring sawtooth of varying voltage output signal is produced, reflecting the relaxation-oscillator nature of a nystagmus condition. As shown, a frequency detector 55 is connected for response to the signal produced at 53, so that nystagmus rate may be displayed at viewable rate-indicating means 56. This rate, as observed, may be utilized by the individual treating himself, or by his assisting companion as an indication of how much to adjust the temperature-offset control 33 (33') at means 31 (31'), for example, to reduce the magnitude of the offset as nystagmus rate is observed to decline, with eventual termination of the treatment when the nystagmus rate (or period) has reduced to a predetermined low level (e.g., period of at least 30 seconds); alternatively, and as shown in FIG. 4, the rate-indicative voltage output of detector means 55 may be supplied directly to each of the temperature-control means 31—31', it being understood that the respective senses of the control by such output voltage will be connected at 31 to produce temperature offsets at 15 which are substantially equal and opposite to those at 15', all with respect to the body or reference temperature. In this latter alternative, FIG. 5 further shows a "Zero"-frequency detector 57 connected to the output of means 53 to make an automatic determination when a predetermined "Zero" rate has been achieved, as (for the above example) a nystagmus period of at least 30 seconds. Upon such determination detector 57 will be understood to produce an output signal to an indicator 58 and/or to shut-down relay means (suggested at 59) for actuating the means 24–30 to OFF condition; in FIGS. 1 and 2, a dashed-line interconnection 59 of the ON/OFF means 24–30 will be understood to suggest the mechanical coordination of such relay means.

In the electrode mask 50, the electrodes A through E may be of metal foil, adhered to the body of the mask and preferably carrying a small adhered absorbent wad (e.g., of cotton) which is impregnated with a conductive paste or salve, each such electrode being protected and kept in readiness for use by a peelable sealing cover tape. The mask can be readied for reuse, by squeezed application of such paste at each electrode.

FIG. 5 shows an alternative mask 60, being intended for disposal after a single use. Prior to use, the mask 60, which may be of thin tough pliable material such as mylar film, is peelably adhered to a flat rectangular cardboard carrier 61, with electrodes A through F facing and therefore sealed against the carrier. Conductive connections to the electrodes are shown by dashed lines, which are suggestive of foil connections between upper and lower plies or laminations of the mylar film. At one corner, a suitable multi-contact plug fitting 62 independently accommodates the separate electrode-lead connections, to the end that simple removable attachment may be made to the mating connector 63 of a flexible-cable connection to the signal-processing means 53. A pressure-sensitive adhesive coating on that surface of the mask which mounts the electrodes not only enables the mask to be peelably removable from carrier 61, but also enables adherence of the mask to the skin when in use, it being understood of course that the thus coated area of the mask is such as to avoid adhesive contact with electrode areas or with any salve-impregnated wadding which may form part of each electrode.

It will be seen that the described invention meets all stated objects with easily applied portable apparatus that can be safely applied by the victim to himself, or by whomever happens to be his companion at onset of an attack. The extent to which prescribed apparatus can be simplified (e.g., prescription of apparatus of FIG. 1 vs. that of FIG. 2, with or without the automation feature of FIG. 4, and with or without presetting of otherwise variable controls) will depend upon the severity of the attacks, upon the ability of the victim to correctively and promptly respond to his recognition of onset symptoms of an attack, and upon the interpretative decision of the prescribing physician. And it will be understood that to accommodate the further prescription of certain physicians, a chart recorder with suitably clocked time base may function directly from the output of signal-processing means 53 to provide a permanent record of each nystagmus condition, its duration, severity and abatement, all as suggested by simple legend at output connection 65 in FIG. 4.

While the invention has been described in detail for preferred embodiments, it will be understood that modifications may be made without departure from the scope of the invention.

What is claimed is:

1. Portable caloric gas-flow therapeutic apparatus for treatment of a nystagmus condition in a patient, comprising a first portable unit including a source of pressurized gas and an electric battery source and separate control means for regulating the outputs of said sources, a second portable unit having means for patient-head support at the region of an ear, said second unit including a speculum nozzle having an outlet poised for discharge into the ear when thus supported, conduit means connecting said nozzle to the control means associated with said gas source and including a flexible conduit between said units, said conduit means including at said second unit electrical heating means adjacent the inlet to said nozzle, and flexible conductor means between said units and connecting said heating means to the control means associated with said battery source.

2. Apparatus according to claim 1, in which at least one of said control means includes a selectively adjustable control element accessible externally of said one unit for patient access in the course of self-administered therapy.

3. Apparatus according to claim 1, in which the control means associated with said battery source includes an electrical heat-sensing element positioned between said heating means and said nozzle for electrical response to temperature of heated gas supplied to said nozzle.

4. Apparatus according to claim 1, wherein said gas source is a container of gas under pressure, and wherein the control means associated with said gas source includes a reducing valve whereby gas passing therethrough is enabled to cool by reason of expansion due to pressure reduction.

5. Apparatus according to claim 4, wherein the range of control by the control means associated with said battery source is such that at said nozzle a first heated-gas temperature below patient-body temperature is achieved for a first control condition thereof and that at said nozzle a second heated-gas temperature above patient-body temperature is achieved for a second control condition thereof.

6. Apparatus according to claim 5, in which selectively operable means is associated with the control means associated with the battery source and is operative to select one of said control conditions.

7. Apparatus according to claim 1, in which said second portable unit includes means for patient-head support of a second speculum nozzle at the region of the patient's other ear, said second nozzle being also connected to the conduit means associated with said gas source, said last-mentioned connection including second electrical heating means adjacent the inlet to said nozzle, and second flexible conductor means between said units and independently connecting said second heating means to the control means associated with said battery source.

8. Apparatus according to claim 7, wherein the range of control by the control means associated with said battery source is such that at one nozzle location a first heated-gas temperature below patient-body temperature is achieved for a first control condition thereof and that at the other nozzle a second heated-gas temperature above patient-body temperature is achieved for a second control condition thereof.

9. Apparatus according to claim 8, wherein the control means associated with said battery source is operative to produce said first and second control conditions concurrently.

10. Apparatus according to claim 8, wherein the control means associated with said battery source is operative to produce said first and second control conditions in alternation.

11. Apparatus according to claim 1, wherein the control means associated with said battery source includes detector means responsive to a nystagmus condition of the patient to produce an electrical signal in accordance therewith, means connected to and responsive to the output of said detector means for producing a signal indicative of the frequency of the nystagmus condition, said last-defined means having a control connection to the control means associated with said battery source.

12. Apparatus according to claim 11, in which the operative sense of said control connection is to reduce the difference between nozzle-flow temperature and patient-body temperature as the observed nystagmus frequency decreases.

13. Apparatus according to claim 12, in which said means responsive to the output of said detector means includes a detector of predetermined minimum or effectively zero frequency, and in which said last-defined means is operative to indicate achievement of said minimum or effectively zero frequency.

14. Apparatus according to claim 1, in which said gas source is a container of gas under pressure, and in which said control means associated with said gas source includes pressure-reducing means whereby gas passing therethrough is enabled to cool by reason of expansion due to pressure reduction, and safety relief-valve means intermediate said pressure-reducing means and said speculum nozzle, said relief valve means being preset to vent gas flow to the atmosphere upon detection of a predetermined safety limit of pressure.

15. Apparatus according to claim 1, in which said control means associated with said gas source includes a flow-regulating valve, and safety relief-valve means intermediate said pressure-reducing means and said speculum nozzle, said relief-valve means being preset to vent gas flow to the atmosphere upon detection of a predetermined safety limit of pressure.

* * * * *